(12) United States Patent
Song et al.

(10) Patent No.: US 11,992,475 B1
(45) Date of Patent: May 28, 2024

(54) APPLICATION OF Z-LIGUSTILIDE IN RESISTING ROTAVIRUSES

(71) Applicant: GUANGDONG MEDICAL UNIVERSITY, Dongguan (CN)

(72) Inventors: Lijun Song, Dongguan (CN); Wenchang Zhao, Dongguan (CN)

(73) Assignee: GUANGDONG MEDICAL UNIVERSITY, Dongguan (CN)

( * ) Notice: Subject to any disclaimer, the term of this patent is extended or adjusted under 35 U.S.C. 154(b) by 0 days.

(21) Appl. No.: 18/544,621

(22) Filed: Dec. 19, 2023

(30) Foreign Application Priority Data

Feb. 8, 2023 (CN) .......................... 202310085052.2

(51) Int. Cl.
*A61K 31/365* (2006.01)
*A61P 31/14* (2006.01)

(52) U.S. Cl.
CPC ............ *A61K 31/365* (2013.01); *A61P 31/14* (2018.01)

(58) Field of Classification Search
CPC .............................. A61K 31/365; A61P 31/14
See application file for complete search history.

(56) References Cited

FOREIGN PATENT DOCUMENTS

CN 109498617 A 3/2019

OTHER PUBLICATIONS

Xie et al., Z-ligustilide: A Review of its Pharmacokinetics and Pharmacology, 34 Phytotherapy Res., 1966-1991 (2020) (Year: 2020).*
Li gui-sheng et al. "Extraction of essential oil from Angelica sinensis by supercritical-CO2 fluid in comparison with that by steam distillation" Chinese traditional and Herbal Drugs. vol. 32, Issue 7, 2001, p. 581-583.
CNIPA, Notification of First Office Action for Chinese application CN202310085052.2, Jul. 26, 2023.
CNIPA, Notification to grant patent right for Chinese application CN202310085052.2, Aug. 3, 2023.

* cited by examiner

*Primary Examiner* — Timothy R Rozof
(74) *Attorney, Agent, or Firm* — Zhigang Ma

(57) ABSTRACT

The present invention discloses an application of Z-ligustilide in resisting rotaviruses, and relates to the technical field of medicines. Z-ligustilide has no drug toxicity to cells at 60-95 μM and can effectively inhibit rotavirus biosynthesis at 70-85 μM. Z-ligustilide plays a role in resisting rotavirus biosynthesis by inhibiting structural protein VP6, and has no effect of adsorbing and directly killing rotaviruses, which provides a new way for resisting rotaviruses.

3 Claims, 7 Drawing Sheets

APPLICATION OF Z-LIGUSTILIDE IN RESISTING ROTAVIRUSES

TECHNICAL FIELD

The present invention relates to the technical field of medicines, and more particularly relates to an application of Z-ligustilide in resisting rotaviruses.

BACKGROUND

Rotavirus (RV) is a double-stranded RNA virus of reoviridae, which is the main pathogen causing diarrhea in infants under 5 years old. RV is highly infectious and pathogenic. At present, there is a lack of specific clinical drugs, the commercially available vaccines are limited and expensive, and the range of preventing strains is limited due to variability and diversity of RV strains.

Therefore, how to effectively prevent and control rotaviruses is a problem to be urgently solved by those skilled in the art.

SUMMARY

In view of this, the present invention provides an application of Z-ligustilide in resisting rotaviruses.

Z-ligustilide is a phthalide compound, with the chemical structure as follows:

Z-ligustilide mainly exists in the volatile oil of Chinese herbs such as Chinese angelica and chuanxiong rhizome. Researches show that Z-ligustilide has pharmacological activities of resisting inflammation, easing pain, resisting atherosclerosis, resisting oxidative stress, resisting senile dementia, resisting tumor, protecting nerve, inhibiting myocardial hypertrophy, and resisting osteoporosis and osteoarthritis and has an inhibitory effect on bacteria such as *Staphylococcus aureus, Bacillus subtilis, Escherichia coli* and *Enterobacter sakazakii* and fungi such as *Aspergillus niger* and *Saccharomyces cerevisiae*, but the anti-rotavirus effect of Z-ligustilide has not been reported.

To achieve the above purpose, the present invention adopts the following technical solution:

An application of Z-ligustilide in preparation of anti-rotavirus agents.

The research of the present invention shows that Z-ligustilide further inhibits rotavirus biosynthesis by inhibiting the gene expression of the rotavirus VP6, so as to achieve the effect of preventing and controlling rotaviruses.

Preferably, the effective concentration of Z-ligustilide is 70-85 μM, and preferably 80 μM.

Another purpose of the present invention is to provide an application of Z-ligustilide in preparation of agents against diseases caused by rotaviruses.

Preferably, the effective concentration of Z-ligustilide is 70-85 μM, and preferably 80 μM.

Another purpose of the present invention is to provide an anti-rotavirus agent, comprising Z-ligustilide.

Preferably, the effective concentration of Z-ligustilide is 70-85 μM, and preferably 80 μM.

Preferably, the agent also comprises pharmaceutically acceptable excipients.

Preferably, the agent is in a form of solid, semi-solid or liquid.

Preferably, the agent is non-aqueous solution, suspension, lozenges, capsules, tablets, granules, pills or powders.

It can be known from the above technical solution that compared with the prior art, the present invention discloses and provides an application of Z-ligustilide in preparation of anti-rotavirus agents. Z-ligustilide has no drug toxicity to cells at 60-95 μM and can effectively inhibit rotavirus biosynthesis at 70-85 μM. Z-ligustilide plays a role in resisting rotavirus biosynthesis by inhibiting structural protein VP6, and has no effect of adsorbing and directly killing rotaviruses.

DESCRIPTION OF DRAWINGS

To more clearly describe the technical solutions in the embodiments of the present invention or in the prior art, the drawings required to be used in the description of the embodiments or the prior art will be simply presented below. Apparently, the drawings in the following description are merely the embodiments of the present invention, and for those ordinary skilled in the art, other drawings can also be obtained according to the provided drawings without contributing creative labor.

DETAILED DESCRIPTION

Figure 1:
FIG. 1 shows normal MA104 cells.

The technical solution in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiment 1

1. Materials and Instruments are Shown in Table 1.

TABLE 1

| Material Name | Manufacturer |
|---|---|
| Z-Ligustilide | Shanghai Macklin Biochemical Co., Ltd. |
| MA104 cell line | Sun Yat-sen University Cell Library |
| Wa strain RV | Third Military Medical University, Immunology Institute |
| 1 × PBS phosphate buffer | Jiangsu Beyotime Biotechnology Institute |
| Cellular dimethyl sulfoxide | American GIBCO company |
| Fetal bovine serum | American GIBCO company |
| High-glucose DMEM culture solution | American GIBCO company |
| 0.25% trypsin digestion solution | Beijing Solarbio Science & Technology Co., Ltd. |
| 0.25% trypsin digestion solution with EDTA | Beijing Solarbio Science & Technology Co., Ltd |
| Penicillin-streptomycin solution (double antibody) | Beijing Solarbio Science & Technology Co., Ltd |
| Confocal dish | Beijing Labgic Technology Co., Ltd. |
| Pipette tip | Shanghai Kirgen Biotechnology Co., Ltd. |
| Cell culture flask | American Corning-Coster company |
| Cell culture dish | American Corning-Coster company |
| Culture plate | American Corning-Coster company |
| Ordinary optical microscope | Japanese OLYMPUS company |
| Inverted fluorescent microscope | Japanese NIKON company |
| Micropipettor | Germany Eppendorf company |
| −20° C. refrigerator | Midea company |
| −80° C. ultra low temperature refrigerator | Thermo Scientific company |
| $CO_2$ incubator | Thermo Scientific company |
| Autoclave | Japanese Sanyo company |
| Super clean bench | Suzhou Airtech company |
| Electric-heated thermostatic water bath | Shanghai Yiheng Science and Technology Co., Ltd. |
| Multimode reader | Gene Company Limited |
| Nucleic acid protein analyzer | Germany Eppendorf company |
| Living cell imager | Thermo Scientific company |
| Illumination incubator | Shanghai Yiheng Science and Technology Co., Ltd. |
| Thermal cycler | T100 Bio-Rad company |
| PCR instrument | Thermo Scientific company |
| High-speed freezing centrifuge | Germany eppendorf company |
| Vortex shaker | Ika Instrument and Equipment Co., Ltd. |
| Liquid nitrogen container | Chart Biology Co., Ltd. |

2. Preparation Methods for Main Reagents:

Z-ligustilide mother solution: 5.2 mg of Z-ligustilide standard product with purity ≥98% is weighed; 1 ml of cellular DMSO is added in a super clean bench for dissolving; the drug solution is filtered through a 0.22 µM filter membrane with a disposable sterile needle for sterilization; and 1 mM of mother solution is prepared.

DMEM medium (containing 10% fetal bovine serum and 1% double antibody): 50 ml of fetal bovine serum and 5 ml of double antibody are successively added to a 400 ml high-glucose DMEM medium in the super clean bench, thoroughly mixed evenly, and then packaged into labeled 50 ml centrifuge tubes; and the centrifuge tubes are sealed, and stored at 4° C.

10 µg/mL pancreatin without EDTA: 0.25% trypsin digestion solution without EDTA and DMEM medium without fetal bovine serum are diluted to 10 µg/mL at a volume ratio of 1:250.

RV growth maintenance medium: 10 µg/mL pancreatin without EDTA and DMEM medium without fetal bovine serum are diluted to 1 µg/mL at a volume ratio of 1:10.

Embodiment 2

Morphological Change of MA104 Cells Infected with Rotaviruses

The RV is melted in a water bath at 37° C. and pretreated with trypsin for 30 min, the virus solution is added to MA104 cells that grow to 80%-90%, and no serum is added to a cell culture medium used for RV infection. The MA104 cells infected with viruses generate cytopathic effect (CPE). When the degree of CPE reaches 75%, the MA104 cells are frozen in a refrigerator at −20° C. After the freezing and melting processes are repeated for 3 times, the MA104 cells are centrifuged at low temperature, and the supernatant is collected, which is the virus solution. The above process is repeated, and the RV is amplified.

Figure 2:
FIG. 2 shows MA104 cells that have been infected with rotaviruses for 48 h.

As shown in FIG. 1, the normal MA104 cells are triangular or fusiform, and the cell outlines are clear. As shown in FIG. 2, the MA104 cells infected with the RV have obvious CPE, the cell boundaries become blurred, the distance between the cells is increased, and finally, the cells completely come off and float.

Embodiment 3

Toxicity of Z-Ligustilide to MA104 Cells (MTT Assay)

According to the common drug concentration range of Z-ligustilide, the cytotoxicity pre-experiment is performed in the range of 1-100 µM in this experiment. The MA104 cells at the logarithmic phase are observed under a microscope, the cellular morphology is uniform and full with clear edges, and when the number reaches 80%, digestion, centrifugation and re-suspension are conducted. After further dilution, 10 µl of the suspension is taken on a blood cell counting plate to count and calculate the required cell volume. Then, the cells are laid in a 96-well plate, 100 µl of cell suspension is added in each well, and the cell density is $8 \times 10^4$ cells/mL. When the cells adhere to the wall to form a single layer, the drug group is administered, and the normal group is added with an equal volume of DMEM (without serum). After incubation for 48 h, the cytotoxicity of Z-ligustilide is detected by MTT reagent. 1/10 volume of MTT solution is added in each well and incubated in an incubator. After 4 h, the solution in the wells is sucked out, 150 µL of DMSO is added in each well, and the absorbance is measured and recorded at a wavelength of 490 nm under the condition of oscillation for 30 s.

The formula of the relative survival rate of the cells is:

$$\{(A_{experimental\ group} - A_{blank})/(A_{control\ group} - A_{blank}) \times 100\%\}$$

Figure 3:
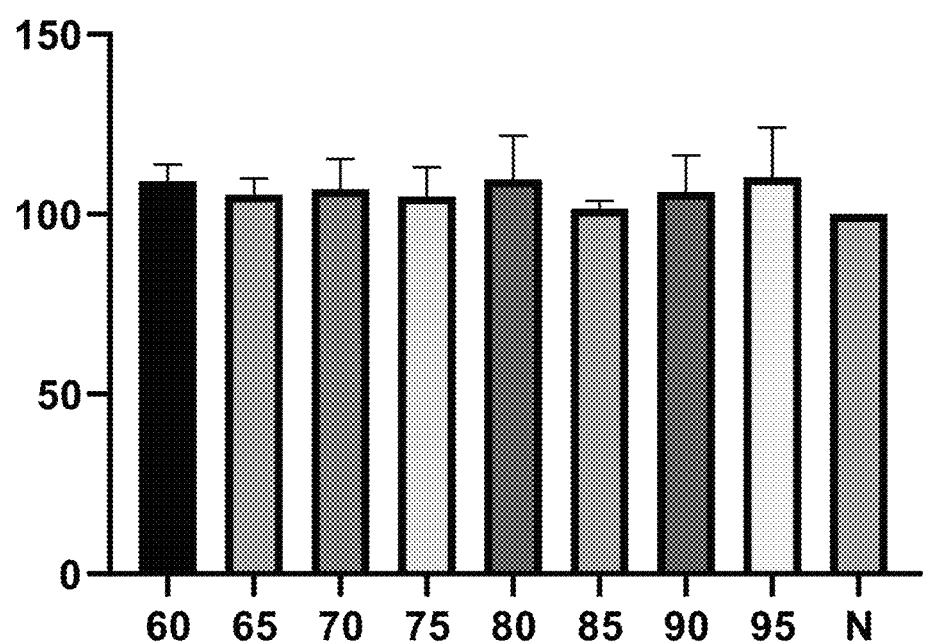
FIG. 3 shows the effect of toxicity of Z-ligustilide to cells (the N group represents the untreated group)

As shown in FIG. 3, Z-ligustilide has no drug toxicity to the cells and has an average survival rate of more than 95% at a drug concentration of 60-95 µM. The drug group has no significant difference in cell viability from the normal group when the concentration of Z-ligustilide is 65-90 µM. Therefore, the selected experimental drug concentration of Z-ligustilide is 65-90 µM.

Embodiment 4

Mechanism of Z-Ligustilide Against Rotaviruses

To investigate whether Z-ligustilide has an effect of resisting RV infection in vitro, MA104 cell models are studied from three aspects of resistance to RV adsorption, direct killing and biosynthesis of Z-ligustilide.

1. Effect of Z-Ligustilide in Resisting RV Adsorption

The drug solution is added in a 96-well culture plate of MA104 cells that grow to a single layer, and each drug solution is added in 6 wells at an amount of 100 μL/well. An equal volume of ribavirin is added to the positive control group, and only an equal volume of DMEM culture solution (without serum) is added to the normal cell control group and the viral control group. Incubation is conducted in 5% $CO_2$ at 37° C. for 2 h. The drug solution is sucked out. Except the normal cell control group, 100TCID50 virus is added (the virus acts with 10 μg/mL pancreatin at 37° C. for 30 min) at an amount of 100 μL/well. Incubation is conducted in 5% $CO_2$ at 37° C. for 2 h. The virus is sucked out, the cell maintenance medium is added at an amount of 200 μL/well. Incubation is conducted in 5% $CO_2$ at 37° C. for continuous observation. After culture for 48 h, an MTT kit is used for detection. 1/10 volume of MTT solution is added in each well and incubated in an incubator. After 4 h, the supernatant is sucked out, DMSO is added, and the absorbance is measured and recorded at a wavelength of 490 nm. The experiment is repeated for 3 times.

Figure 4:
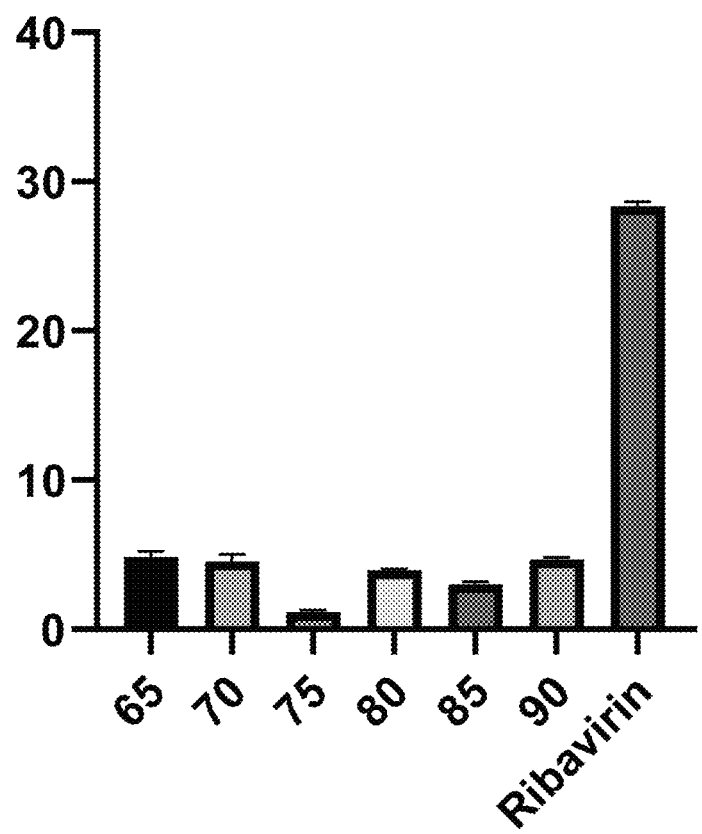
FIG. 4 shows the effect of Z-ligustilide in resisting RV adsorption (compared with the ribavirin group, ****$p<0.0001$)

As shown in FIG. 4, compared with ribavirin, the Z-ligustilide group has inhibition rates against RV of 4.85%, 4.55%, 1.14%, 3.95%, 3.01% and 4.69% at 65-90 μM, with statistical difference, but the maximum inhibition rate is only about 4.85%, which indicates that Z-ligustilide has no obvious effect of resisting RV adsorption.

2. Effect of Z-Ligustilide in Directly Killing RV

The drug is mixed with 100TCID50 virus solution (the virus acts with 10 μg/mL pancreatin for 30 min) at an equal volume to act for 2 h. After the cells are washed twice with PBS, the cells are added in a 96-well culture plate of MA104 cells that grow to a single layer. The same operation as above is conducted for ribavirin and RV in the positive control group, and only an equal volume of DMEM is added to the normal cell control group and the viral control group. Incubation is conducted in 5% $CO_2$ at 37° C. for 2 h, the mixed solution is sucked out, and the cell maintenance medium is added at an amount of 100 μL/well. Incubation is conducted in 5% $CO_2$ at 37° C. for continuous observation. After continuous culture for 48 h, an MTT kit is used for detection. 1/10 volume of MTT solution is added in each well and incubated in an incubator. After 4 h, the supernatant is sucked out, DMSO is added, and the absorbance is measured and recorded at a wavelength of 490 nm. The experiment is repeated for 3 times. The viral inhibition rate of the drug is calculated.

The formula of the viral inhibition rate is:

$$\{(A_{drug\ group} - A_{virus\ group})/(A_{normal\ group} - A_{virus\ group}) \times 100\%\}$$

Figure 5:
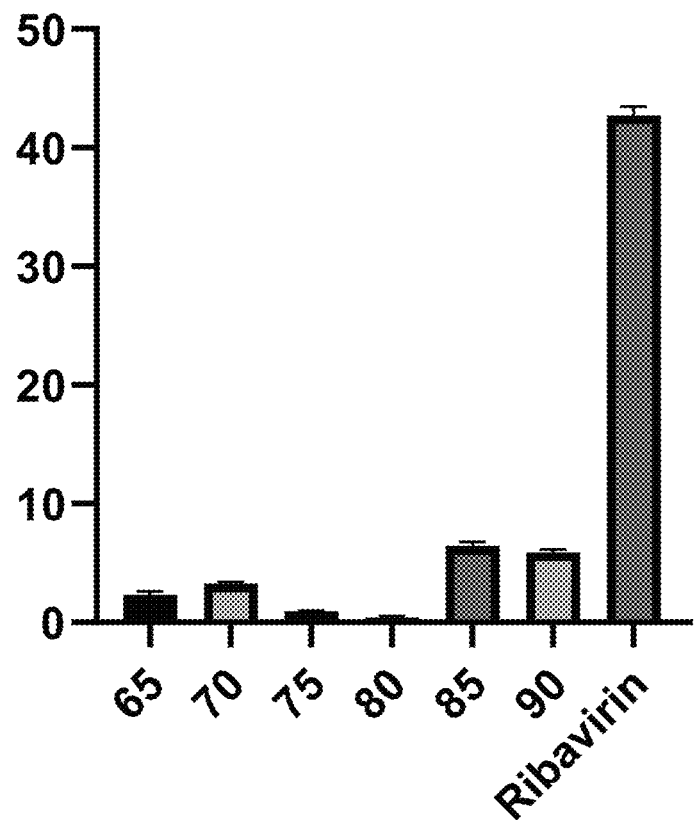
FIG. 5 shows the effect of Z-ligustilide in directly killing RV (compared with the ribavirin group, ****$p<0.0001$)

As shown in FIG. 5, compared with the ribavirin group, each Z-ligustilide group has low inhibition rates against RV, respectively 2.32%, 3.25%, 0.93%, 0.4%, 6.45% and 5.89% at concentrations of 65-90 μM, with statistically significant difference, which indicates that Z-ligustilide has no obvious effect of directly killing RV.

3. Effect of Z-Ligustilide in Resisting RV Synthesis

100TCID50 virus solution (the virus acts with 10 μg/mL pancreatin for 30 min) is added in a 96-well culture plate of MA104-2 cells that grow to a single layer, at an amount of 100 μL/well. The cells have been washed twice with PBS. A normal cell control group is set, and added with an equal volume of DMEM culture solution. Incubation is conducted in 5% $CO_2$ at 37° C. for 2 h, the virus solution is sucked out, and drug solution and ribavirin of different concentrations are added respectively at an amount of 100 μL/well. A viral control group is set, and only added with the cell maintenance medium at an amount of 100 μL/well. Incubation is conducted in 5% $CO_2$ at 37° C. for continuous observation. After continuous culture for 48 h, an MTT kit is used for detection. 1/10 volume of MTT solution is added in each well and incubated in an incubator. After 4 h, the supernatant is sucked out, DMSO is added, and the absorbance is measured and recorded at a wavelength of 490 nm. The experiment is repeated for 3 times. The viral inhibition rate of the drug is calculated.

Figure 6:
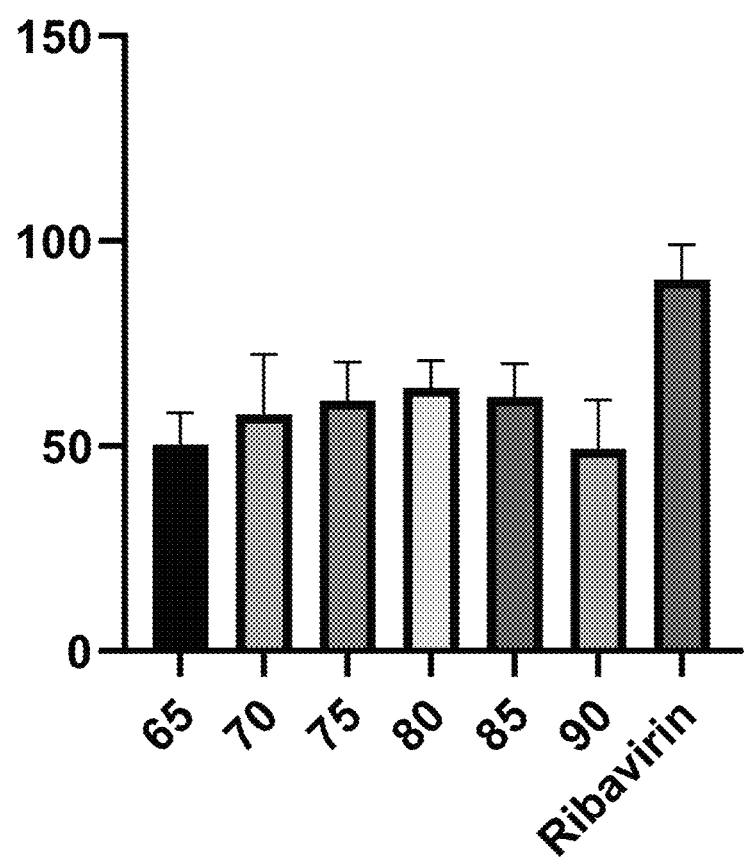
FIG. 6 shows the effect of Z-ligustilide in resisting RV biosynthesis (compared with the ribavirin group, *$p<0.05$, and **$p<0.01$)

As shown in FIG. 6, compared with the ribavirin group, Z-ligustilide has an inhibition rate against RV of more than 50% at 70-85 μM, with statistical difference, wherein the inhibition rate against RV reaches 64.21% at 80 M, without statistical difference from the ribavirin group, which indicates that Z-ligustilide has an effect of inhibiting RV biosynthesis.

Embodiment 5

Influence of Z-ligustilide on gene expression level of structural protein VP6 of RV (1) Extraction and quantification of total RNA ① To further verify whether Z-ligustilide has an effect of inhibiting RV synthesis, after Z-ligustilide inhibits RV synthesis for 48 h, drug groups of low, medium and high concentrations, the ribavirin group, the N group and the RV group are selected, the supernatant is removed, the solution is washed twice with PBS, 1 ml of Trizol reagent is added, and then the solution is collected into a 1.5 mL enzyme-free EP tube after standing for 5 min. 200 μL of chloroform is added in the tube. After vortex oscillation for 15 s, the solution is stood at room temperature for 3 min, and centrifuged (4° C., 12000 r/min, 15 min). The centrifuged sample is divided into three layers: a colorless upper layer, a white middle layer and a red lower layer.

② The supernatant is carefully sucked into a new 1.5 mL enzyme-free EP tube (with a volume of about 500 μL), and an equal volume of pre-cooled isopropanol is added. The solution is shaken up and down violently, mixed well, stood at 4° C. for 10 min, and centrifuged (4° C., 12000 r/min, 10 min).

③ After centrifugation, white precipitate can be seen at the bottom of the EP tube. The supernatant is removed, and the precipitate is retained. 1 mL of the prepared 75% ethanol solution (prepared from anhydrous ethanol and enzyme-free water at a ratio of 3:1) is added, shaken and mixed well, and centrifuged (4° C., 12000 r/min, 5 min). The supernatant is discarded, and the solution is stood at room temperature for 15-20 min for drying.

④ After drying, 20 μL of DEPC water is added in the EP tube, and the tube wall is gently blown to dissolve RNA. The RNA concentration of the sample is determined by a NanoDrop micro ultraviolet spectrophotometer, and then the sample can be used directly for the experiment or stored at −80° C. for later use.

(2) Reverse transcription reaction of mRNA

① Reaction for Removal of Genomic DNA

A reaction mixture is prepared on ice according to the following components in a reaction volume of 20 μL in accordance with the instructions of Evo M-MLV RT Kit with gDNA Clean for qPCR II. The consumables used in the experiment are all Axygen enzyme-free consumables.

TABLE 2

Reaction System for Removal of Genomic DNA

| Component Name | Addition |
|---|---|
| gDNA Clean Reagent | 1 μL |
| 5 × gDNA Clean Buffer | 2 μL |
| Total RNA[*1] | — |
| RNase free water | Up to 10 μL |

[*1] The amount of RNA can be added as needed. In a 20 μL reverse transcription system, a maximum of 1 μg of total RNA is used; and when a probe method is used, a maximum of 2 μg of total RNA is used.

Reaction conditions: 42° C. 2 min, 4° C.

② Reverse Transcription Reaction

The reaction solution is prepared according to the following table, and the reverse transcription reaction is performed.

TABLE 3

Reverse Transcription Reaction System

| Component Name | Addition |
|---|---|
| Reaction solution in step 1) | 10 μL |
| Evo M-MLV RTase Enzyme Mix | 1 μL |
| RT Primer Mix | 1 μL |
| 5 × RTase Reaction Buffer Mix I | 4 μL |
| RNase free water | 4 μL |
| Total | 20 μL |

Reaction conditions: 37° C. 15 min, 85° C. 5 sec, 4° C.

(3) Real Time PCR reaction

Real time quantitative PCR is used to detect the control group and the RVWa strain-infected group by SYBR Green I fluorescent labeling. SYBR® Green Premix Pro Taq HS qPCR Kit II is used, and GAPDH is selected as the internal reference. In the experiment, dedicated real-time eight-row PCR tubes for Axygen are used for preparing a real-time fluorescence quantitative PCR amplification reaction system according to the following table, and the reaction solution is prepared on ice (the total reaction system is 10 μL).

TABLE 4

PCR Reaction System

| Component Name | 10 μL system |
|---|---|
| 2X SYBR ® Green Pro Taq HS Premix II | 5 μL |
| CDNA | 1 μL |
| Primer F | 0.2 μL |
| Primer R | 0.2 μL |
| RNase free water | Up to 10 μL |

TABLE 5 qPCR Reaction Conditions

| | Temperature | Time | Number of Cycles |
|---|---|---|---|
| Step 1 | 95° C. | 30 sec | 1 |
| Step 2 | 95° C. | 5 sec | |
| | 60° C. | 30 sec | 40 |
| Step 3 | Dissociation stage | | |

TABLE 6

Primer Sequences

| Gene | | Primer (5'-3') |
|---|---|---|
| GAPDH | Forward | CTGGTGACCCGTGCTGCTT, SEQ ID NO. 1 |
| | Reverse | TTTGCCGCCTTCTGCCTTA, SEQ ID NO. 2 |
| VP6 | Forward | GACCACCAAACATGACACCA, SEQ ID NO. 3 |
| | Reverse | CATCGGCGAGTACAGACTCA, SEQ ID NO. 4 |

Figure 7:
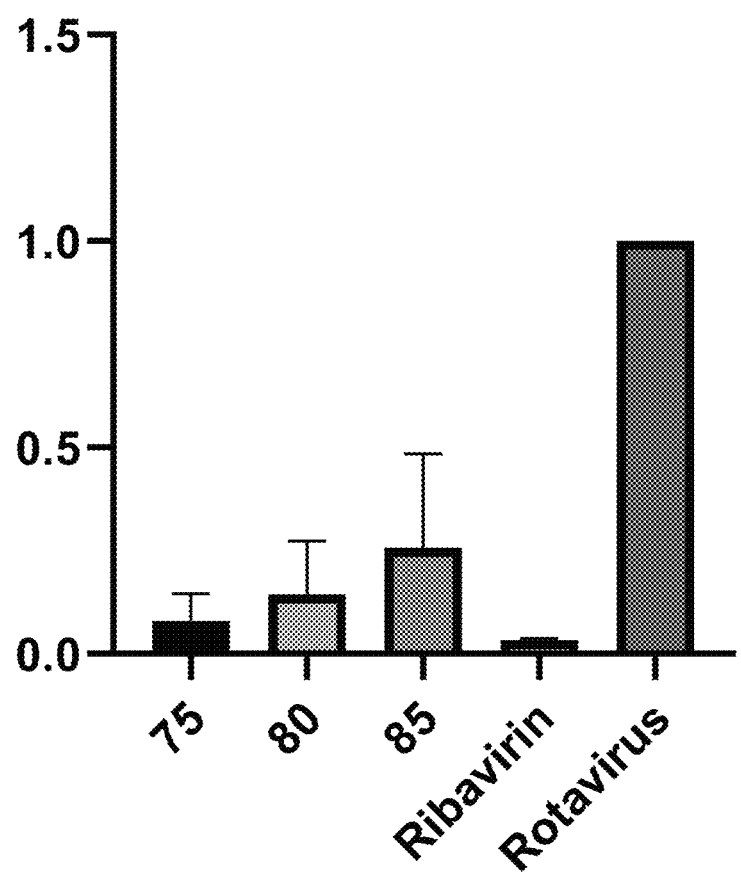
FIG. 7 shows the influence of Z-ligustilide on the gene expression of structural protein VP6 of RV-infected MA104 cells (compared with the rotavirus group, **$p<0.01$).

The results are shown in FIG. 7. Compared with the RV group, the Z-ligustilide group has the VP6 expression level significantly decreased at concentrations of 75 μM, 80 μM and 85 μM, wherein Z-ligustilide inhibits VP6 expression most significantly at 75 μM, which indicates that Z-ligustilide plays a role in resisting RV by inhibiting gene expression of VP6.

Each embodiment in the description is described in a progressive way. The difference of each embodiment from each other is the focus of explanation. The same and similar parts among all of the embodiments can be referred to each other.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention. Therefore, the present invention will not be limited to these embodiments shown herein, but will conform to the widest scope consistent with the principle and novel features disclosed herein.

What is claimed is:

1. A method of inhibiting rotavirus biosynthesis, comprising: providing Z-ligustilide, wherein an effective concentration of the Z-ligustilide is 70-85 μM.

2. The method of claim 1, wherein the effective concentration of the Z-ligustilide is 80 μM.

3. The method of claim 1, wherein the step of providing a Z-ligustilide comprises: dissolving a Z-Ligustilide material by adding DMSO (Dimethyl sulfoxide) to obtain a solution, filtering and sterilizing the solution to obtain the Z-ligustilide.

\* \* \* \* \*